(12) United States Patent
Gorbunov

(10) Patent No.: US 10,458,946 B2
(45) Date of Patent: Oct. 29, 2019

(54) ION SELECTING DEVICE FOR IDENTIFICATION OF IONS IN GASEOUS MEDIA

(71) Applicant: ANCON TECHNOLOGIES LIMITED, Canterbury (GB)

(72) Inventor: Boris Zachar Gorbunov, Canterbury (GB)

( * ) Notice: Subject to any disclaimer, the term of this patent is extended or adjusted under 35 U.S.C. 154(b) by 0 days.

(21) Appl. No.: 15/919,582

(22) Filed: Mar. 13, 2018

(65) Prior Publication Data

US 2018/0266990 A1  Sep. 20, 2018

(30) Foreign Application Priority Data

Mar. 16, 2017  (GB) .................................. 1704180.7

(51) Int. Cl.
  *G01N 27/62*  (2006.01)
  *H01J 49/06*  (2006.01)

(52) U.S. Cl.
  CPC ......... *G01N 27/622* (2013.01); *G01N 27/624* (2013.01); *H01J 49/061* (2013.01)

(58) Field of Classification Search
  USPC ........................................ 250/286, 287, 283
  See application file for complete search history.

(56) References Cited

U.S. PATENT DOCUMENTS 5,869,831 A  2/1999  De La Mora et al.
6,787,763 B2  9/2004  De La Mora et al.
(Continued)

FOREIGN PATENT DOCUMENTS

WO  03/041114 A2  5/2003
WO  2011/020034 A1  2/2011

OTHER PUBLICATIONS

G. Reid Asbury, Jorg Klasmeier, Herbert H. Hill Jr. Analysis of explosives using electrospray ionization:ion mobility spectrometry (ESI:IMS) Talanta 50 (2000), pp. 1291-1298.
(Continued)

*Primary Examiner* — Kiet T Nguyen
(74) *Attorney, Agent, or Firm* — Heslin Rothenberg Farley & Mesiti P.C.

(57) ABSTRACT

The invention provides a method of separating and collecting ions of a predetermined ion mobility from a gaseous mixture of ions of different ion mobilities using a differential mobility analyser apparatus, wherein the differential mobility analyser apparatus comprises an ion-separation chamber having:
  (a) a sample gas flow inlet;
  (b) a focusing chamber, an opening at one end of which serves as the sample gas flow inlet through which sample gas can flow into the ion-separation chamber;
  (c) a sheath gas inlet connected or connectable to a supply of sheath gas;
  (d) a sheath gas outlet;
  (e) an ion outlet through which the ions of predetermined ion mobility can be collected; and
  (f) two or more electrodes arranged to provide an ion-separating electric field across the ion-separation chamber;
wherein the focusing chamber is oriented at an angle of from 30° to 90° relative to a direction of flow of the sheath gas along the ion-separation chamber;
and wherein a focusing zone is provided in the focusing chamber, the focusing zone comprising at least two surfaces where a non-uniform density of electric charge can be created;

(Continued)

the method of separating and collecting ions of predetermined ion mobility comprising:

(i) introducing a stream of sheath gas through the sheath gas inlet at a predetermined flow rate;

(ii) introducing a stream of sample gas containing an ion cloud into and through the focusing chamber and through the focusing zone therein at a predetermined flow rate;

(iii) subjecting the ion cloud in the sample gas in the focusing zone to a non-uniform electric field generated by the non-uniform density of electric charge such that the electric field modifies ion trajectories in the sample gas so that they converge to produce an ion stream of reduced width;

(iii) directing the stream of sample gas containing the ion stream of reduced width from the focusing chamber through the sample gas flow inlet into the ion-separation chamber; and (iv) selecting a field strength for the ion-separating electric field so as to attract ions of a predetermined ion mobility to the ion outlet.

Also provided is differential mobility analyser apparatus for separating and collecting ions of a predetermined ion mobility from a gaseous mixture of ions of different ion mobilities using a differential mobility analyser apparatus, wherein the differential mobility analyser apparatus comprises an ion-separation chamber having:

(a) a focusing chamber connected or connectable to a supply of sample gas containing ions of interest;

(b) a sheath gas inlet connected or connectable to a supply of sheath gas;

(b) a sheath gas outlet;

(c) an ion outlet through which the ions of predetermined ion mobility can be quantified or collected; and (d) two or more electrodes arranged to provide an ion-separating electric field across the ion-separation chamber;

wherein the sample gas inlet is oriented at an angle of from 30° to 90° relative to a direction of flow of the sheath gas along the ion-separation chamber;

and wherein the apparatus is configured to provide a focusing zone in the focusing chamber, the focusing zone comprising at least two surfaces where a non-uniform density of electric charge is created so as to generate a non-uniform electric field that modifies ion trajectories in a sample gas passing through the focusing chamber and through the focusing zone so that they converge to produce an ion stream of reduced width;

the apparatus comprising a controller that enables the ion-separating electric field to be varied to attract ions of a predetermined ion mobility to the ion outlet.

17 Claims, 4 Drawing Sheets

(56) References Cited

U.S. PATENT DOCUMENTS

| | | | |
|---|---|---|---|
| 7,449,683 | B2 | 11/2008 | Shvartsburg et al. |
| 7,855,360 | B2 | 12/2010 | Fernandez de la Mora et al. |
| 7,928,374 | B2 | 4/2011 | Rus-Perez et al. |
| 9,523,657 | B2 | 12/2016 | Wu |
| 2005/0006578 | A1 | 1/2005 | Rockwood et al. |
| 2006/0054804 | A1 | 3/2006 | Wexler |
| 2007/0278398 | A1 | 12/2007 | Li |
| 2008/0251714 | A1* | 10/2008 | Juan ............ G01N 27/622 250/288 |
| 2013/0009053 | A1 | 1/2013 | Wu |

OTHER PUBLICATIONS

Jan C. T. Eijkel, Herbert Stoeri and Andreas Manz. A dc Microplasma on a Chip Employed as an Optical Emission Detector for Gas Chromatography. Anal. Chem. 2000, 72, 2547-2552.

J. Fernandez de la Mora, Ionization of vapor molecules by an electrospray cloud, International J. Mass Spectrom., 300. 182-193 (2011).

J Zhao, F Eisele, M Titcombe, C Kuang, p. McMurry, Chemical Ionization mass spectrometric measurements of atmospheric neutral clusters using the cluster-CIMS, J. Geophys. Res., 115 (2010), 1-19.

H. Goldstein, I. E. Galbally, Known and unexplored organic constituents in the Earth's Atmosphere, Environmental Sci. & Tech., Mar. 1, 2007, pp. 1515-1521.

J. Rus; D. Moro; J.A. Sillero; J. Royuela, A. Casado, J. Fernández de la Mora, IMS-MS studies based on coupling a Differential Mobility Analyzer (DMA) to commercial API-MS systems, Int. J. Mass Spectrom, 298, 30-40 (2010).

C. Wu, W.F. Siems, H.H. Hill Jr., Secondary electrospray ionization ion mobility spectrometry/mass spectrometry of illicit drugs, Anal. Chem. 72 (2000) 396-403.

E. Mesonero, J.A. Sillero, M. Hernandez, J. Fernández de la Mora, Secondary electrospray ionization (SESI) detection of explosive vapors below 0.02 ppt on a Triple quadrupole with an atmospheric pressure source (2009).

P. Martinez-Lozano, J. Rus, G. Fernandez de la Mora, M. Hernandez and J. Fernandez de la Mora, JASMS, p287, 2009.

Poster Presented at the ASMS Annual Conference, May 31-Jun. 4, 2009, Philadelphia, PA, 2009, http://www.seadm.com/descargas/Poster_Api%205000_09_EMS%203.pdf.

Vidal-de-Miguel, G., Macia, M., Pinacho, P., Blanco, J., Low-Sample Flow Secondary Electrospray Ionization: Improving Vapor Ionization Efficiency, Anal. Chem. 84(20), 8475-8479, 2012.

M. Amo-Gonzalez, J. Fernandez de la Mom. *High Dynamic Range Differential Mobility Analyzer (DMA) Coupled with a Mass Spectrometer and a nano-ElectroSpray Ionization Source*. Submitted to J. Am. Soc. Mass Spectr., Sep. 2016.

C. J. Hogan, B. Ruotolo, C. Robinson, J. Fernandez de la Mora. Tandem Differential Mobility Analysis-Mass spectrometry Reveals Partial Gas-Phase Collapse of the GroEL Complex, J. Phys. Chem. B, 115(13), 3614-3621, 2011.

C. Larriba-Andaluz and J. Fernandez de la Mora, Gas Phase Structure of Coulombically Stretched Polyethylene Glycol Ions., *J. Phys. Chem. B*, 116, 593-598, 2012.

E. Criado, J. Fernández-García, J. Fernández de la Mora, Mass and charge distribution analysis in negative electrosprays of large polyethylene glycol chains by Ion Mobility Mass Spectrometry, Anal. Chem., 85(5), 2710-2716, 2013.

Fernández-Garcia, J.; Fernández de la Mora, J. *Measuring the Effect of Ion-Induced Drift-Gas Polarization on the Electrical Mobilities of Multiply-Charged Ionic Liquid Nanodrops in Air, J. Am. Soc. Mass Spectrom.,* 24:1872-1889 (2013).

Qinghua Zhou, Liying Peng, Dandan Jiang, Xin Wang, Haiyan Wang & Haiyang Li, Detection of Nitro-Based and Peroxide-Based Explosives by Fast Polarity-Switchable Ion Mobility Spectrometer with Ion Focusing in Vicinity of Faraday Detector. Nature Scientific Reports | 5:10659 | DOI: 10.1038/srep10659 (2015).

G.A. Eiceman, Ion-mobility spectrometry as a fast monitor of chemical composition, Trends In Analytical Chemistry, 2002, pp. 259-275, vol. 21, No. 4, Elsevier Science B.V.

P. Martinez-Lozano, J. Fernández de la Mora(2006) Resolution improvements of a nano-DMA operating transonically, J. Aerosol Sci., v. 37, pp. 500-512.

Santos J. P., E. Hontanon, E. Ramiro and M. Alonso(2009) Performance evaluation of a high-resolution parallel-plate differential mobility analyser. Atmos. Chem. Phys., v.9, pp. 2419-2429.

(56) References Cited

OTHER PUBLICATIONS

Steer B., B. Gorbunov, R. Muir, A. Ghimire and J. Rowles (2014) Portable Planar DMA.

M. Alonso, J. Santos, E. Hontanon, E. Ramiro, First Differential Mobility Analysis (DMA) Measurements of Air Ions Produced by Radioactive Source and Corona, Aerosol and Air Quality Research, 9: 453-457, (2009).

M. Labowsky, J. Fernandez de la Mora, Novel ion mobility analyzers and filters, Aerosol Science 37 (2006) 340-362.

UKIPO search report for UK patent application No. 1704180.7, dated Jul. 13, 2017.

* cited by examiner

ION SELECTING DEVICE FOR IDENTIFICATION OF IONS IN GASEOUS MEDIA

CROSS REFERENCE TO RELATED APPLICATIONS

This application claims priority from UK patent application No: 1704180.7, filed on Mar. 16, 2017, the entire contents of which are hereby incorporated by reference herein.

This invention relates to a method and apparatus for selecting ions of a particular predetermined ion mobility from a mixture containing ions and electrically neutral molecules. More particularly, the invention enables the extraction of ions of interest from a sample gas flow so that they can be directed into a clean gas flow where they can be quantified. The method provides more effective separation, increases the resolution of the ion-selecting device and therefore enables the quantification of complex mixtures at low concentrations of molecules of interest in gases.

BACKGROUND OF THE INVENTION

Quantification of compounds at trace levels in the air often requires separation of a complex mixture and selecting molecules of interest for analysis. One technique used for this purpose for the separation of ions at atmospheric pressure is Ion Mobility Spectrometry (IMS), see for example G. A. Eiceman, Ion-mobility spectrometry as a fast monitor of chemical composition, Trends In Analytical Chemistry). IMS is widely used for many security applications, for example to detect explosives in airports.

Differential Mobility Analyser (DMA) technology has been used to separate electrically charged aerosol particles in the air, see e.g. Steer et al. (2014). Recently this method has been extended to the separation of ions at atmospheric pressure; see for example Martinez-Lozano and de la Mora (2006) or Santos at al. (2009).

US2005/0006578 discloses a type of DMA in the form of a cross-flow ion mobility analyser (CIMA) comprising at least two electrodes disposed so as to create an electric field therebetween, and a gas flow that opposes the electric field. Ions are carried through a channel by the gas flow and ions of a specific mobility are trapped by the opposing electric field and flow field within the channel and are detected when the ions reach the end of the channel. A detector at the end of the channel sees a continuous stream of mobility-selected ions, the ions being selected by modifying the electric field and/or the velocity of the flow field.

Another cross-flow DMA is disclosed in US 2006/0054804 A1 which provides a system for performing ion or particle mobility spectrometry. The system operates by first receiving a sample for analysis. Next, the system ionizes the sample and injects the ionized sample into a laminar gas flow. An electric field crosses the laminar gas flow so that the laminar gas flow and the electric field combine to spatially separate ions of the analytes based on ion mobility and so that the spatially separated ions contact different elements of an electrometer array. The system then analyses the output of the electrometer array to determine the mobility of the analytes.

A DMA device comprises an ionisation chamber, a separation chamber and an electric current measuring means. A sample of air containing molecules of interest is ionised in the ionisation chamber. The ions are then drawn into the separation chamber via an inlet. In the separation chamber, a linear electric field applied across the velocity flow spatially separates ions of different mobility. At the opposite electrode of the separation chamber, an outlet is positioned at some distance from the inlet. The apparatus is set up so that only ions of particular mobility can reach the outlet and progress on to an ion current measuring device which can be, for example, an electrometer based upon the Faraday cup where ions impinge on the collector and carry an electric charge so that an ion current can be measured. Variation in the electric field enables ions of different mobilities to be directed to the outlet. Thus, by measuring ion currents are various field strengths, ion mobility spectra can be recorded.

There is an increasing demand for more sensitive explosives detection technologies for a wide range of homeland security applications, particularly transport security. The low vapour pressure of some explosives presents challenges to current IMS devices. An even greater challenge is to detect concealed explosives in small quantities. However, a major problem with detecting and quantifying chemicals at very low concentrations is that, at such low concentrations, background signals from interfering chemical compounds become more prominent and this can lead to false positive signals being detected. To overcome this problem, higher resolution ion selecting means are required.

In U.S. Pat. No. 7,928,374 B2 a DMA was interfaced with an atmospheric pressure ionization mass spectrometer (APCI-MS) to improve ion identification and resolution. This improves resolution but a mass spectrometer is a large expensive device and along with a DMA the system becomes too large and expensive for many applications.

A known type of DMA apparatus is shown in FIG. 1 below. It is known that the resolving power (Rp) of a DMA of the type shown in FIG. 1 can be defined as the ratio of the sheath gas flow rate (Qsh) to the ion sample flow rate (Qi): Rp=Qsh/Qi. In a DMA of the type shown in FIG. 1, the resolution provided by the instrument is not influenced by the geometry, for example by the gap between the electrodes that create the ion-separating electric field (shown schematically in FIG. 1 below as electrodes (6) and (7)) or by the distance between the baffle (3) and the lower electrode (7). The resolving power is however influenced by the ratio of the gap between electrodes to the thickness of the bundles of ion trajectories in a sample gas flow. The ion and neutral molecule trajectories are governed by the continuous media laws of motion that lead to an expression Rp=Qsh/Qi. Thus, to reduce the thickness of the bundles of ion trajectories, it is necessary to increase the sheath gas flow rate Qsh or/and decrease the ion sample flow rate Qi.

In practice, in order to increase the resolution Rp, the sheath flow is increased. To achieve a resolving power of sufficient magnitude for practical applications, the sheath flow typically needs to be much greater than the ion sample flow, with the result that the velocity field created by the sheath gas flow in a DMA can often be close to the speed of sound. This creates two significant problems. Firstly, creating such high sheath gas flow rates requires powerful and therefore large and expensive pumps. Secondly, it leads to high Reynolds numbers and thus the flow in the DMA becomes turbulent. The turbulence has a profound effect on the resolving power by reducing it due to the formation of eddies and increasing broadening of the ion trajectories. To increase Rp by reducing the sample flow is not desirable either because it decreases the number of ions coming out of the DMA and therefore decreases the sensitivity.

THE INVENTION

The present invention provides a conceptually different way of improving ion selection and increasing resolving power by the use of a focusing ion inlet to the DMA that narrows ion trajectories and avoids or reduces the need to increase the sheath flow rate.

Accordingly, in one aspect, the invention provides a method of separating ions of a predetermined ion mobility from a gaseous mixture of ions of different ion mobilities using a differential mobility analyser apparatus, wherein the differential mobility analyser apparatus comprises an ion-separation chamber having:

(a) a sample gas flow inlet;
(b) a focusing chamber, an opening at one end of which serves as the sample gas flow inlet through which sample gas can flow into the ion-separation chamber;
(c) a sheath gas inlet connected or connectable to a supply of sheath gas;
(d) a sheath gas outlet;
(e) an ion outlet through which the ions of predetermined ion mobility can be collected; and
(f) two or more electrodes arranged to provide an ion-separating electric field across the ion-separation chamber;

wherein the focusing chamber is oriented at an angle of from 30° to 90° relative to a direction of flow of the sheath gas along the ion-separation chamber;
and wherein a focusing zone is provided in the focusing chamber, the focusing zone comprising at least two surfaces where a non-uniform density of electric charge can be created;
the method of separating ions of predetermined ion mobility comprising:

(i) introducing a stream of sheath gas through the sheath gas inlet at a predetermined flow rate;
(ii) introducing a stream of sample gas containing an ion cloud into and through the focusing chamber and through the focusing zone therein at a predetermined flow rate;
(iii) subjecting the ion cloud in the sample gas in the focusing zone to a non-uniform electric field generated by the non-uniform density of electric charge such that the electric field modifies ion trajectories in the sample gas so that they converge to produce an ion stream of reduced width;
(iii) directing the stream of sample gas containing the ion stream of reduced width from the focusing chamber through the sample gas flow inlet into the ion-separation chamber; and
(iv) selecting a field strength for the ion-separating electric field so as to attract ions of a predetermined ion mobility to the ion outlet.

In most known types of DMA (for example as illustrated in FIG. 1), the sample gas stream enters the ion-separation chamber such that its direction of flow is aligned with the direction of flow of the sheath gas. This is achieved by means of a baffle that guides the sample gas stream so that it flows in a direction substantially parallel of the sheath gas flow before merging with the sheath gas flow at the end of the baffle. One significant difference between known DMA apparatuses and methods of separating ions and the method and apparatus of the present invention is that, in the present invention, there is no baffle guiding the sample gas flow in a parallel direction to the sheath gas flow. Instead, the sample gas passes through a focusing chamber which is oriented at an angle of from 30° to 90° relative to a direction of flow of the sheath gas along the ion-separation chamber and directly out through the sample gas inlet into the ion-separation chamber. This means that the sample gas stream enters the ion-separation chamber at an angle of at least 30° and up to 90° with respect to the direction of flow of the sheath gas.

More typically the focusing chamber is oriented at an angle of from 45° to 90° relative to the direction of flow of the sheath gas along the ion-separation chamber, preferably from 60° to 90°, more preferably from 75° to 90°, and most preferably at an angle of approximately 90° relative to the direction of flow of the sheath gas along the ion-separation chamber.

The references to the orientation of the focusing chamber refer to the direction of the centre line or flow axis of the focusing chamber at the point where it opens out into the ion-separation chamber; i.e. at the sample gas inlet.

The invention makes use of an essentially non-uniform focusing electric field generated by a non-uniform density electric charge. The electric field has a component that is orientated predominantly across the sample gas flow and has the property of modifying the trajectories of ions in the sample gas flow so that they converge, i.e. they move closer to a central line extending through the focusing zone.

The non-uniform density electric charge can be a region of high localised charge. The regions of localised charge can be provided by electrodes arranged within the focusing chamber. A non-uniform focusing electric field can be created by two or more spaced apart charged regions of the same polarity, e.g. a pair of spaced apart positively charged regions. The two or more spaced apart regions bearing the same charge polarity create opposing electric fields. Ions of the same polarity passing through the opposing electric fields are therefore subjected to repelling forces that cause them to move towards a centre point between the spaced apart charged regions, or to a point where the repelling effects of the spaced apart charged regions balance out.

The extent to which the trajectories of the ions are modified as they pass through the focusing electric field will depend on both the strength of the electric field and the time spent by the ions in the electric field, which is turn will depend to at least some extent on the flow rate of the sample gas through the electric field. If the sample gas flow rate is too high, the ions will not be exposed to the electric field for long enough to have a significant effect on their trajectories. Therefore, the sample gas flow rate is selected so as to allow the ions to be exposed to the electric field for long enough for focusing to take place.

The phenomenon of the modification of the ion trajectories so that they converge to give an ion stream of reduced width may be referred to herein as "convolution" and the act of modifying the ion trajectories so that they converge in this way may be referred to as "convoluting".

A first convoluting criterion that defines the relationship between the sample flow rate, sheath gas flow rate, the length of the separation DMA chamber (a parameter that is indirectly linked to the electric field strength: for example, for ions of mobility in the range from 0.8 to 2.5 cm²/V/s where V is the potential difference that determines the electric field strength) and the geometry of the focusing zone may be expressed as follows:

$$(Hin/L)*(Qsh/Qi) > Pf$$

where $Hin$ is the width of the focusing chamber, $L$ is the length of the ion separation chamber, $Qsh$ is the sheath gas flow rate, $Qi$ is the sample gas flow rate and $Pf$ is a focusing factor which preferably lies within the limits $1 < Pf < 30$. This expression that is based upon experimental observations of the performance of DMAs of different geometries working in various regimes. It shows unexpectedly that the geometry of the inlet affects focusing and therefore the resolving power.

As indicated above, the flow rate of the sample gas (which equates to Qi in the above expression) affects the length of time that the ions are exposed to the focusing electric field and hence the extent to which the trajectories of the ions are modified. Also, the width of the sample gas flow (which equates to Hin in the above expression) will determine the initial width or thickness of the stream of ions moving towards the ion-separation chamber. The greater the width of the sample gas flow, the greater the extent of focusing required to give good resolution.

Thus, for example, experiments performed with sample flows of different widths (Hin) have shown how the resolving power is influenced by the geometry of the inlet, see Table 1 below.

TABLE 1

Resolving power measured for various Hin in experiments with Acetonitrile ions in Nitrogen (L = 10 mm, Qsh = 4 l/min and Qi = 0.25 l/min were constant).

| Hin (mm) | Rp, measured | Conventional Rp = Qsh/Qi |
| --- | --- | --- |
| 0.1 | 14 | 16 |
| 0.2 | 16 | 16 |
| 0.4 | 18 | 16 |
| 0.8 | 21 | 16 |
| 1.5 | 22 | 16 |
| 3.0 | 21 | 16 |

As shown in Table 1, an increase in Hin from 0.1 mm to 3 mm gives an increase in the resolving power from 14 to 21. This effect cannot be explained in terms of a conventional DMA where Rp=Qsh/Qi=16. The accuracy of measuring Rp was ±1.2. Thus small deviations in measured Rp at 0.1 and 3.0 mm can be explained by the accuracy of measurements.

The method of the invention makes use of an electric field, a component of which is oriented across the sample gas flow and diverts from the periphery of the sample gas flow towards the centre of the flow. Provided that the aforementioned convoluting criterion is fulfilled, then ions in the sample flow will be urged to the centre of the flow forming a narrow ion trajectory bundles without any need to increase the sheath flow rate. The method of the invention is so effective that it enables the formation of a very narrow ion flow even when there is no sheath gas flow, although of course in practice a sheath gas flow is employed when using the method for the separation and collection of ions of differing ion mobilities.

It should be noticed that the convolution criterion contains, in addition to the two parameters that control the ion trajectories bundle thickness in a conventional DMA (i.e. Qsh and Qi), two additional parameters (Hin and L) that determine the focusing of ions according to the present invention. Conformity with the convolution criterion enables improved resolution by the DMA through the increase in value of another ratio, Hin/L. In a conventional device the resolution is influenced only by the ratio Qsh/Qi. This is another dimension allowing improving resolution without increasing Qsh so much that air flow in the DMA chamber becomes turbulent. This enables the device to be smaller, cheaper and provide higher resolution.

In another aspect, the invention provides a differential mobility analyser apparatus for separating and collecting ions of a predetermined ion mobility from a gaseous mixture of ions of different ion mobilities using a differential mobility analyser apparatus, wherein the differential mobility analyser apparatus comprises an ion-separation chamber having:

(a) a focusing chamber connected or connectable to a supply of sample gas containing ions of interest;
(b) a sheath gas inlet connected or connectable to a supply of sheath gas;
(b) a sheath gas outlet;
(c) an ion outlet through which the ions of predetermined ion mobility can be collected; and
(d) two or more electrodes arranged to provide an ion-separating electric field across the ion-separation chamber;

wherein the sample gas inlet is oriented at an angle of from 30° to 90° relative to a direction of flow of the sheath gas along the ion-separation chamber;

and wherein the apparatus is configured to provide a focusing zone in the focusing chamber, the focusing zone comprising at least two surfaces where a non-uniform density of electric charge is created so as to generate a non-uniform electric field that modifies ion trajectories in a sample gas passing through the focusing chamber and through the focusing zone so that they converge to produce an ion stream of reduced width;

the apparatus comprising a controller that enables the ion-separating electric field to be varied to attract ions of a predetermined ion mobility to the ion outlet.

In both the method and apparatus aspects of the invention, the arrangement of the sheath gas inlet and outlet and focusing chamber and outlet, and the electrodes that generate ion separation electric field is typically such that the direction of flow of the sheath gas is at an angle with respect to the sample gas inlet. For example, the focusing chamber may be oriented at an angle of from 45° to 90° relative to the direction of flow of the sheath gas along the ion-separation chamber, preferably from 60° to 90°, more preferably from 75° to 90°, and most preferably at an angle of approximately 90° relative to the direction of flow of the sheath gas along the ion-separation chamber.

As with the method of the invention as defined above, the apparatus of the invention typically makes use of an ion trajectories convolution zone including a focusing chamber (which may also be referred to herein as an ion inlet well) adjacent the ion-separation chamber with at least two surfaces where a non-uniform density of electric charge can be created and through which the sample flow can be directed. The non-uniform density of electric charge gives rise to an essentially non-uniform focusing electric field having a component that is orientated predominantly across the sample flow and has the property of being able to convolute ion trajectories in the sample gas flow through the focusing chamber so that ions move closer to the central line of the convolution zone.

A second convoluting criterion that defines a relationship between the sample gas flow rate, the electric field strength or in practice the potential difference and the geometry of the focusing zone can be expressed as follows:

$$\left(1 + \frac{\Delta Vin}{\Delta Zin} \cdot \frac{H}{\Delta V}\right) \cdot \frac{Hin}{L} \cdot \frac{Qsh}{Qi} > P_f$$

where Hin is the thickness of the sample ion flow, L is the length of the DMA chamber, H is the gap between the electrodes of the ion-separation chamber, ΔV is the potential difference between the electrodes of the ion-separation chamber, Qsh is the clean sheath gas flow, Qi is the sample gas flow, ΔVin is the potential difference on the surface of the sample inlet, ΔZin is the depth of the convolution zone well where the potential difference ΔVin is applied and Pf is the focusing factor. Typically for the focusing factor, Pf falls with the range (1<Pf<40).

It will be appreciated that when, in the second convoluting criterion, ΔVin=0, this corresponds to the first convoluting criterion.

The focusing (convolution) zone can take a number of different forms.

The focusing (convolution) zone can be created by bundles of electric charges located at an end of the focusing chamber, i.e. where the opening at the end of the focusing chamber serves as the sample gas inlet. For example, the opening at the end of the focusing chamber may coincide with a slot or gap or notch in one of the electrodes of the ion-separation chamber so that edges of the electrode form a rim to the opening and provide the bundles of electric charges required to create the focusing electric field. It will be appreciated that, in this embodiment, the electric field created by the electric charges will extend both in an upstream direction back along the focusing chamber and also out into the interior of the ion-separation chamber.

Alternatively, or additionally, one or more electrodes may be positioned in the focusing chamber at a distance ΔZin back from the opening at the end of the chamber.

In one embodiment, the focusing zone is provided by an electrically conductive strip located in a wall of the focusing chamber, wherein the electrically conductive strip has a potential difference ΔVin applied thereto. The strip is insulated by a surrounding electrical insulator from any other internal conductive surfaces of the focusing chamber and is positioned at a location Zin from the opening at the end of the focusing chamber. The vertical dimension or width of the strip is ΔZin. The insulator also insulates the strip from the electrodes in the ion separation chamber. Suitable values for ΔZin, the co-ordinate Zin and the voltage ΔVin can be found by routine trial and error. This embodiment is advantageous in that has greater focusing efficiency because the additional voltage ΔVin provides an additional boost of focusing electric field in the focusing chamber.

In another embodiment of the apparatus of the invention, the focusing chamber is provided with a plurality of electrically conductive strips located in a wall thereof, wherein each electrically conductive strip has a potential difference ΔVin applied thereto, thereby to generate a focusing electric field, each strip being insulated by a surrounding electrical insulator from any other conductive strips and internal conductive surfaces of the focusing chamber.

Thus, in this embodiment, there are several additional electrically conductive strips (similar to those described in the foregoing embodiment) positioned at particular locations (co-ordinates) Zin, Zinα and Zinβ. Each strip has a potential difference ΔVin, ΔVinα and ΔVinβ applied to it accordingly. The strips are insulated by an electrical insulator from one another and the other internal surfaces of the focusing chamber. The locations of the tops of the strip electrodes relative to the opening at the end of the focusing chamber Zin, Zinα and Zinβ, their vertical dimensions (width) ΔZin, ΔZinα and ΔZinβ and the voltages ΔVin, ΔVinα and ΔVinβ can be determined empirically by trial and error. This embodiment is advantageous in that the additional strips, additional voltages ΔVin, ΔVinα and ΔVinβ each provide an additional boost to the focusing electric field and thereby improve the resolution provided by the apparatus.

It should be recognised that the number of the strips (Ns), vertical dimensions ($\Delta Zin_i$) and their vertical co-ordinates ($Zin_i$) and voltage differences ($\Delta Vin_i$) can be varied; for the number of strips 1<Ns<1000.

In another embodiment, the focusing chamber is provided on an internal surface thereof with a layer of a conductive material which is insulated from the electrodes of the ion-separation chamber by an electrical insulator material and wherein a pair of conductive electrodes is connected to the conductive material and said electrodes are in turn connected to a potential difference source so as to create a desired potential profile along the internal surface of the focusing chamber. Thus for a vertical well, a desirable potential difference V(Z) profile will be created inside the well as a function of Z. This generates a non-uniform electric field with focusing properties to increase resolution.

Thus, in this embodiment, a desired voltage difference along the internal surface of the focusing chamber is created by a layer of a conductive material, e.g. carbon, that is insulated from the electrodes of the ion-separation chamber by an electrical insulator material. At the ends (e.g. top and bottom) of the conductive material are conductive electrodes which are connected to a potential difference source to create the desired potential along the internal surface of the focusing chamber. The dimensions of the layer of conductive material and the voltages applied to it can be selected empirically by trial and error as necessary.

In another embodiment, the walls of the focusing chamber are lined with or formed from a conductive material having low electrical conductivity, for example a conductive glass, conductive ceramic, or carbon film. The use of such materials enables the creation of a linear or non-linear desired potential profile on the walls of the focusing chamber that facilitate ion focusing and therefore improve resolution.

DETAILED DESCRIPTION OF THE INVENTION

The invention will now be described, by way of example, with reference to the accompanying drawings, FIGS. 1 to 7.

Figure 1:
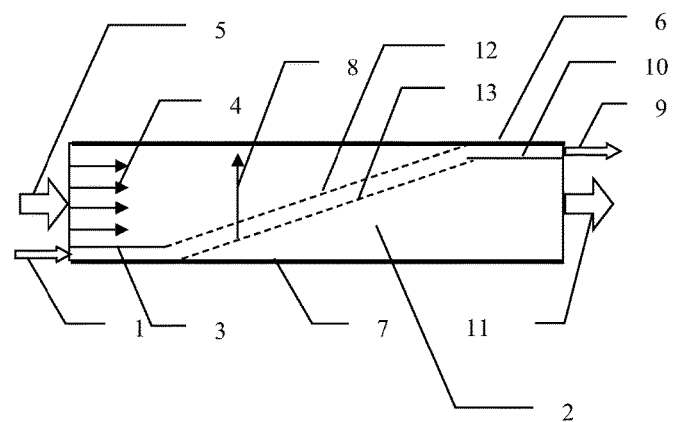
FIG. 1 shows schematically a prior art apparatus for selecting ions in a DMA.

Referring to FIG. 1, there is shown a known type of DMA apparatus having an ion sample inlet (1), leading to an ion separation chamber (2), and a baffle (3) that separates a sample gas flow passing through the sample gas inlet (1) from a clean sheath gas flow (4) introduced via sheath gas flow inlet (5). In the ion separation chamber (2), two electrodes are positioned at the top (6) and the bottom (7) respectively of the ion separation chamber and these generate an electric field (8) which, in use, attracts ions of a selected ion mobility so that their trajectories are diverted by an ion outlet baffle (10) to an ion outlet (9). The ion separation chamber also has an outlet (11) for the sheath gas flow containing unselected ions.

In use, a gaseous sample containing ions of various ion mobilities enters the inlet (1) of the separation chamber (2) where the sample gas flow is initially shielded by the baffle (3) and then joins the flow of sheath gas (4) that has entered the ion separation chamber through the sheath gas flow inlet (5). As soon as the sample gas flow has cleared the baffle (3), the movement of ions in the sample gas is influenced by the electric field (8) with the result that ion trajectories (12) and (13) are diverted from predominantly horizontal streamlines (4) towards the electrode (6). Ions of a predetermined ion mobility will be drawn to the outlet of the selected ions (9) via the section of the chamber (2) adjacent to the second baffle (10). Ions of higher mobility will cross the trajectory line (12) towards the electrode (6) and will be discharged. Ions of lesser mobility will cross the trajectory line (13) and will be carried out with the sheath gas flow towards the sheath flow outlet (11). Scanning the voltage difference between electrode (6) and (7), it is possible to obtain a mobility spectrum of ions in the sample (see for example the spectrum in FIG. 7.

It will be appreciated that FIG. 1 represents a simplified 2D picture of a simplified case of the uniform flow velocity in the ion separation chamber (2). In reality, the velocity profile v(X,Y,Z) is more complicated due to the boundary conditions at the internal surfaces of the chamber: v(X,Y, Z)=0. Here X, Y and Z are Cartesian coordinates inside the chamber (2) where X is the horizontal coordinate along the length of the ion separation chamber, Z is the vertical coordinate along the height of the ion separation chamber and Y is the coordinate orthogonal to X and Z.

The resolving power of the device shown in FIG. 1 is determined by the ratio of the sheath flow rate to the ion sample flow rate Qsh/Qin. Often the ratio of Qin/Qsh is used to characterise the resolution of a DMA because this ratio represents the width of the ion peak in the mobility spectrum. The distance between the baffle 3 and the electrode 7 normally is chosen in accordance with the principle of flow continuity to eliminate the velocity difference between the sample gas flow containing the ions and the sheath flow. The resolution can be expressed as a ratio Qin/Qsh or more often used resolving power Rp=Qsh/Qin. In a conventional DMA, the resolution is not influenced by the geometries of the inlets and outlets.

Figure 2:
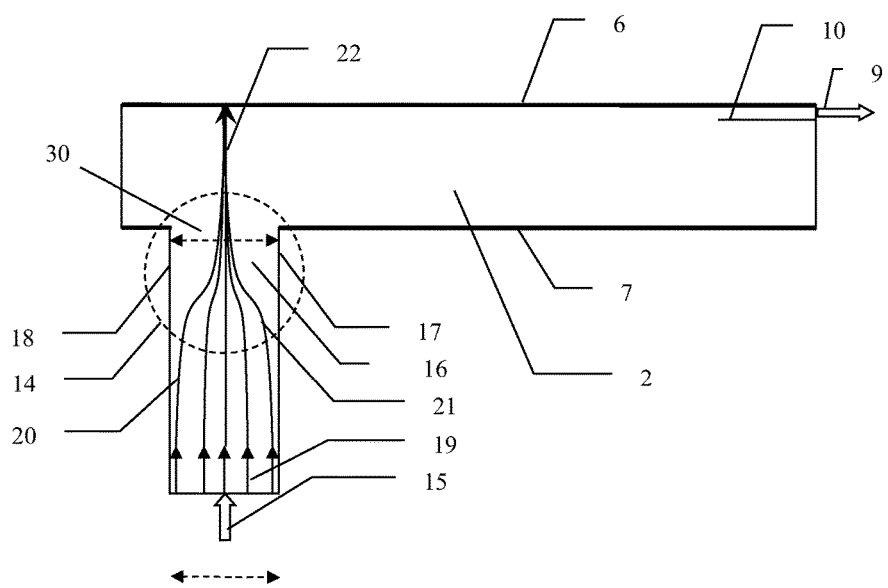
FIG. 2 is a schematic view of an apparatus according to one embodiment of the invention showing the manner in the trajectories of ions in a sample gas are focussed. In the drawing, the sheath flow has been shown as Qsh=0 in order to demonstrate more clearly the principles of operation.

FIG. 2 shows a DMA apparatus according to a first embodiment of the present invention. The drawing in FIG. 2 shows the apparatus without a sheath gas flow in order to demonstrate more clearly the convolution (converging) of ion trajectories in the ion trajectories focusing zone (14). Thus, the DMA apparatus comprises an ion separation chamber (2) connected to a supply of sample gas flow (15) containing ions of interest. An associated means (e.g. a pump) for maintaining the flow rate of the sample gas into the apparatus is not shown. The apparatus further comprises an ion focusing chamber (16) with two surfaces (17) and (18), each having thereon a non-uniform electric charge density distribution, the walls being spaced apart by a distance Hin (shown by the double headed dotted line arrow in FIG. 2), an ion-separation chamber (2) of a DMA with electrodes (6) and (7) including means (not shown) to generate a voltage difference between them and thereby create an electric field for separating ions of interest.

FIG. 2 illustrates the principle of operation of the apparatus 2 when the sheath gas flow is set to zero. In operation without the sheath gas flow, a sample gas flow containing ions enters the inlet (15) of the ion focusing chamber (16) where, at the bottom of the focusing chamber, the ion trajectories are uniform and linear (19). As a result of the electric field created by the charges on the surfaces (17) and (18), the ion trajectories, see for example trajectories (20) and (21), converge (are convoluted) forming a narrow bundle (22) which passes out of the opening (30) ("the sample gas inlet") at the other end of the focusing chamber and moves towards the electrode (6) under the influence of the electric field generated between electrode (6) and (7). The mode of operation of the apparatus of the present invention resulting in the production of a narrow ion bundle that is attracted directly to the opposite electrode (6) is entirely different from the mode of operation of a conventional DMA where, without a sheath gas flow, the sample gas ion flow would fill the greater part of the volume of the DMA chamber.

Figure 3:
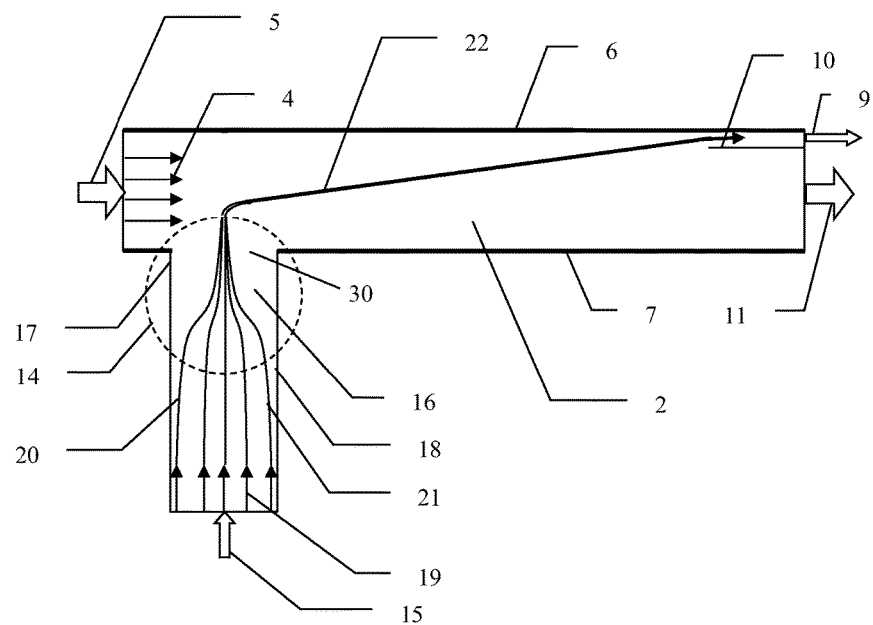
FIG. 3 is a schematic view of the apparatus of FIG. 2 in use for selecting ions. In the Figure, the sheath gas flow is shown.

FIG. 3 shows the apparatus of FIG. 2 but with the sheath gas flow turned on. The apparatus comprises an ion-separation chamber (2) provided with electrodes (6) and (7) and means (not shown) for generating a potential difference between the electrodes so as to create an ion-separating electric field in the ion-separation chamber. The ion-separation chamber has a sheath gas inlet (5), a sheath gas flow outlet (11). Sheath gas passing along the chamber (2) generates a velocity field that move ions towards the selected ion outlet (9).

The apparatus also comprises an ion focusing chamber (16) having an inlet (15) and an outlet (30). The outlet (30) serves as a sample gas inlet for the ion separation chamber. The interior of the ion focusing chamber has a pair of surfaces (17) and (18), spaced apart by a distance Hin, the two surfaces each having a non-uniform electric charge density distribution of the same polarity (e.g. positive charge) thereon. The electric charges on the surfaces (17) and (18) give rise to a non-uniform electric field which acts as a focusing zone (14) for the ions in the sample gas. The inlet (15) of the focusing chamber (16) can be connected to a means (e.g. a pump—not shown) for maintaining a flow of sample gas into the focusing chamber (16).

FIG. 3 illustrates the operation of the apparatus of FIG. 2 with the sheath gas flow turned on. As with the embodiment of FIG. 2, a sample gas containing ions enters the opening (15) into the focusing chamber (16) and travels along the focusing chamber towards the outlet (30) and into the ion-separation chamber (2). As the sample gas passes along the focusing chamber (2), the initial ion trajectories (19) are focused into a narrow bundle of trajectories (22) as described above in relation to FIG. 2. The sheath gas flow (4) enters via the sheath gas inlet (5) and creates a flow of clean gas through the chamber (2). The sample gas flow containing the focused stream of ions moves into the chamber (2) and is carried downstream by the sheath flow gas. As they pass down the chamber (2), the trajectories of the ions are modified by interaction with the electric field and are attracted towards the electrode (6). The extent to which the ions move towards the electrode (6) depends on the strength of the field and the ion mobilities of the ions according to their mobility, as well as the velocity of the combined sheath gas flow and sample gas flow at a given electric field strength, only ions of a particular ion mobility reach the outlet (9). Ions with higher mobility move faster and are neutralised at the surface of the electrode (6). Ions with lower mobility move more slowly and are carried out with the sheath flow into the sheath flow outlet (11). The electric field strength can be adjusted by changing the voltage difference applied to the electrodes (6) and (7) so that ions of a particular ion mobility are collected at the outlet (9). By varying the electric field strength, a spectrum of ions of differing ion mobilities can be obtained. The mode of operation described above is similar to that of a conventional DMA but differs in that the focusing of the ions in the focusing chamber (16) reduces the thickness of the bundle of ion trajectories (22) making it possible to reduce the sheath flow velocity without compromising resolution or improve the resolution without increasing the ratio of the sheath flow rate to the sample flow rate.

In practice, it was observed that the first convolution criterion makes it possible to achieve Rp=30 at a very small sheath flow rate Qsh=4 l/min. This is considerably less that the sheath flow necessary to get the same Rp with a conventional DMA where Qsh>100 l/min is required. Therefore, with a DMA designed according the current invention based upon the convolution criterion, it is possible to build a small and inexpensive portable/handheld device.

The second convolution criterion makes it possible to increase the resolving power even further. Thus a device designed according to the second convolution criterion would demonstrate even higher potential for miniaturisation and increase in resolution.

It should be understood that the convolution criteria and the value of Pf do not predict the resolving power quantitatively. They are to indicate the direction how to increase the Rp. The resolving power is a monotonous function of the focusing factor Rp(Pf) that can be presented in a differential form dRp(Pf)/dPf>0. In general, the link between Pf and Rp is a complicated function and it is not the subject of the invention.

Figure 4:
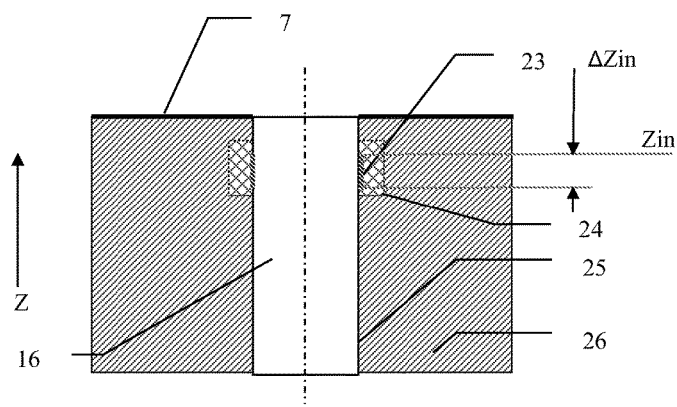
FIG. 4 is a schematic view of an apparatus sample inlet section according to a second embodiment of the invention in which the focusing chamber contains an electrically conducting strip having a potential difference ΔVin which provides or augments the focusing electric field.

There are various ways in which the focusing chamber (16) can be configured to provide a focusing effect. An apparatus according to a second embodiment of the invention includes a focusing chamber with additional means to generate and control focusing of ions. The part of this apparatus with the conductive strip is shown in FIG. 4. In this embodiment, the focusing chamber (16) has an electrically conductive strip (23) to which a potential difference ΔVin is applied. The strip (23) is insulated by an electrical insulator (24) from the rest of the internal surface (25) of the focusing chamber (16). The strip (23) is positioned at a coordinate Zin in the focusing chamber and has a width ΔZin. The insulator (24) also insulates the strip (23) from the rest of the body (26) of the electrode (7) that is kept at the same voltage as the electrode (7). The vertical dimension (width) of ΔZin, the co-ordinate Zin and the voltage ΔVin can be determined empirically by trial and error.

The mode of action of the embodiment of FIG. 4 is similar to that of the embodiment shown in FIGS. 2 and 3, except that the embodiment of FIG. 4 has greater focusing efficiency because of the additional electric field generated by the voltage ΔVin at strip (23).

Figure 5:
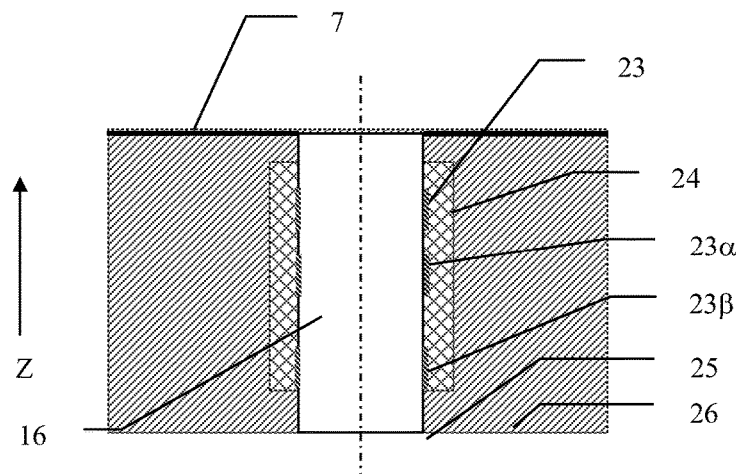
FIG. 5 is a schematic view of an apparatus sample inlet section according to a third embodiment of the invention wherein the focusing chamber has three conductive strips located therein.

In the embodiment of shown in FIG. 5, the focusing chamber (16) is provided with three electrically conductive strips (23), (23α) and (23β) positioned at particular vertical co-ordinates Zin, Zinα and Zinβ. Each strip (23), (23α) and (23β) has a potential difference ΔVin, ΔVinα and ΔVinβ applied to it accordingly. The strips (23), (23α) and (23β) are insulated by the electrical insulator (24) from the rest of the internal surface (25) of the focusing chamber (16). In a simplified version of this embodiment the vertical dimensions (widths) of the strips are equal to each other (ΔZin=ΔZinα=ΔZinβ). The co-ordinates Zin, Zinα and ΔZinα and the voltages ΔVin, ΔVinα and ΔVinβ can be determined empirically by trial and error experimentation.

The mode of action of the embodiment shown in FIG. 5 is similar to that of the embodiments shown in FIGS. 2, 3 and 4 but has the further advantage of providing better focusing efficiency because of the additional electric fields created in the focusing chamber (16) by the voltages ΔVin, ΔVinα and ΔVinβ.

It should be recognised that the number of the strips ($N_s$), vertical dimensions/widths ($\Delta Zin_i$) and their vertical co-ordinates ($Zin_i$) and voltage differences ($\Delta Vin_i$) can be varied. Thus, for example, the number of strips can fall within the range $1 \leq N_s \leq 1000$. More particularly, the number of strips can fall within the range $1 \leq N_s \leq 500$ or within the range $1 \leq N_s \leq 100$ and most particularly, within the range $1 \leq N_s \leq 10$.

Figure 6:
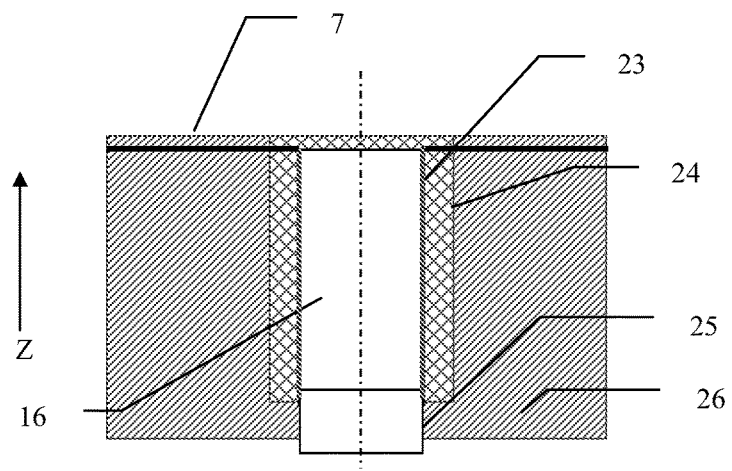
FIG. 6 is a schematic view of an apparatus sample inlet section according to a fourth embodiment of the invention wherein the focusing chamber is lined with a layer of conductive layer to which a potential difference is applied to provide or augment the focusing electric field.
Figure 7:
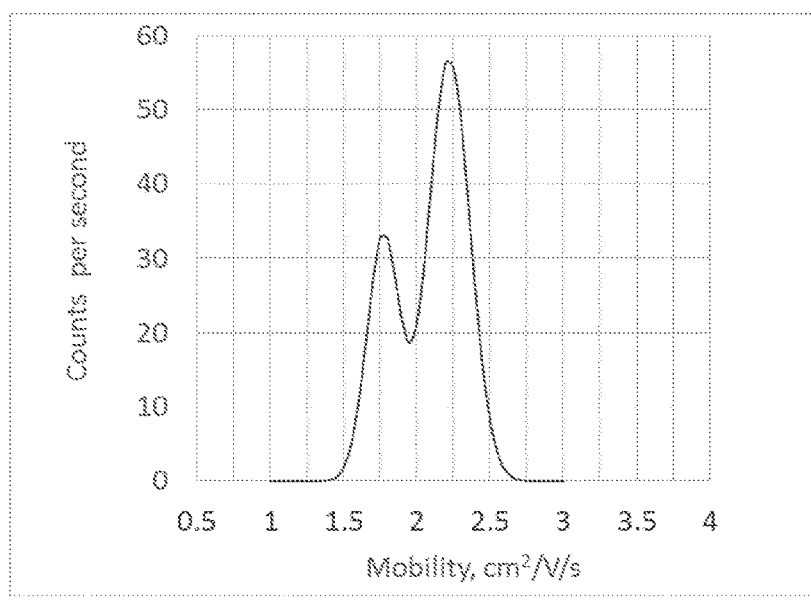
FIG. 7 is an ion mobility spectrum recorded using an apparatus and method of the invention.

Another embodiment of the current invention, shown in FIG. 6, is similar to the embodiment of FIGS. 2, 3, 4 and 5 except that the desired voltage difference along the internal surface of the focusing chamber (16) is created by a layer of a conductive material (23) that is insulated from the rest of electrode material (26) with an electrical insulator (24). The conductive material (23) has two conductive electrodes positioned at, respectively, the top and the bottom of the conductive material (not shown in the FIG. 6). The conductive electrodes are connected to a potential difference source to create a desired potential along the internal surface of the focusing chamber (16). The vertical dimensions and the voltages can be determined empirically by trial and error experimentation.

The conductive material (23) can be made from a thin layer of metal or alloy, e.g. Nickel Chromium. It should be mentioned that other conductive materials including carbon, composite materials, conductive ceramics, conductive glass and conductive plastics can be used. The embodiment of FIG. 6 creates a similar focusing electric field to the embodiments of FIGS. 2, 3, 4 and 5 but is much easier and cheaper to manufacture.

Preferably the conductive material (23) is made from electrically conductive materials or non-conductive materials with an electro conductive layer or inclusions on the surface. Such a layer can be made by metal-plating, vacuum deposition or painting with a conductive paint.

Example

An ion selecting device according to the embodiment shown in FIGS. 2 and 3 was built and tested. Various dimensions of the sample inlet were investigated. All metal parts, including electrode (6) and (7), were manufactured from stainless steel. A 10 mm spacer (partition) between electrodes (6) and (7) was manufactured from PTFE. In one embodiment of the invention the width of the focusing chamber (16) was Hin=1 mm. The gap between electrodes in the DMA chamber (2) was H=8 mm. The length of the selection zone or the distance between the ion inlet and ion outlet was 10 mm. The gap between the top electrode (6) and the outlet baffle (10) at the in outlet (9) was 0.5 mm. There were two porous air-through membranes in the DMA chamber across the sheath flow to reduce the turbulence and create a laminar flow regime, not shown in the drawings. The membranes were positioned on the left from the ion inlet and on the right from the ion outlet and were made of polyamide (Nylon) of 0.5 mm thickness. The outlet baffle was manufactured from stainless steel of 0.2 mm thickness. The remaining dimensions of the apparatus were as described in the publication by Steer et al. (2014) Portable Planar DMA: Development and Tests, Aerosol Science and Technology, v. 48, pp. 250-259, the contents of which are incorporated herein by reference.

The voltage between electrodes was supplied by a saw tooth generator especially designed for the DMA and which enabled a linear voltage change from 1V to 1,000 V to be achieved over the scan time from 10 s to 1,000 s. This enabled a number of counts vs. scan voltage to be recorded using an ion counter of the type described in U.S. Pat. No. 7,372,020. The resulting data can be used to calculate the number of counts vs. electrical mobility. The procedure for this calculation is widely described in technical textbooks, but see also the paper by Steer et al. idem).

A typical spectrum of a sample containing di-isopropyl methyl-phosphonate, recorded with the device described above is shown in FIG. 7. The fact that two peaks are shown demonstrates the high resolution provided by the apparatus of the invention. Without the ion focusing provided by the apparatus of the present invention, the two peaks cannot be resolved.

REFERENCES

U.S. Pat. No. 7,372,020 B2, Ion counter; B. Gorbunov.
G. A. Eiceman, Ion-mobility spectrometry as a fast monitor of chemical composition, Trends In Analytical Chemistry, 2002, pp. 259-275, vol. 21, No. 4, Elsevier Science B.V.
P. Martinez-Lozano, J. Fernandez de la Mora (2006) Resolution improvements of a nano-DMA operating transonically, J. Aerosol Sci., v. 37, pp. 500-512.
Santos J. P., E. Hontanon, E. Ramiro and M. Alonso (2009) Performance evaluation of a high-resolution parallel-plate differential mobility analyser. Atmos. Chem. Phys., v.9, pp. 2419-2429.
US 2005/0006578 A1 Alan L. Rockwood, Edgar D. Lee, Nosa Agbonkonkon, Milton L. Lee.
US 2006/0054804 A1 Anthony S Wexler.
U.S. Pat. No. 7,928,374 B2 Juan Rus-Perez and Juan Fernandez de la Mora.
Steer B., B. Gorbunov, R. Muir, A. Ghimire and J. Rowles (2014) Portable Planar DMA: Development and Tests, Aerosol Science and Technology, v. 48, pp. 250-259.

The invention claimed is:

1. A method of separating and collecting ions of a predetermined ion mobility from a gaseous mixture of ions of different ion mobilities using a differential mobility analyser apparatus, wherein the differential mobility analyser apparatus comprises an ion-separation chamber having:
    (a) a sample gas flow inlet;
    (b) a focusing chamber, an opening at one end of which serves as the sample gas flow inlet through which sample gas can flow into the ion-separation chamber;
    (c) a sheath gas inlet connected or connectable to a supply of sheath gas;
    (d) a sheath gas outlet;
    (e) an ion outlet through which the ions of predetermined ion mobility can be collected; and
    (f) two or more electrodes arranged to provide an ion-separating electric field across the ion-separation chamber;
wherein the focusing chamber is oriented at an angle of from 30° to 90° relative to a direction of flow of the sheath gas along the ion-separation chamber;
and wherein a focusing zone is provided in the focusing chamber, the focusing zone comprising at least two surfaces where a non-uniform density of electric charge can be created;
the method of separating and collecting ions of predetermined ion mobility comprising:
    (i) introducing a stream of sheath gas through the sheath gas inlet at a predetermined flow rate;
    (ii) introducing a stream of sample gas containing an ion cloud into and through the focusing chamber and through the focusing zone therein at a predetermined flow rate;
    (iii) subjecting the ion cloud in the sample gas in the focusing zone to a non-uniform electric field generated by the non-uniform density of electric charge such that the electric field modifies ion trajectories in the sample gas so that they converge to produce an ion stream of reduced width;
    (iii) directing the stream of sample gas containing the ion stream of reduced width from the focusing chamber through the sample gas flow inlet into the ion-separation chamber; and
    (iv) selecting a field strength for the ion-separating electric field so as to attract ions of a predetermined ion mobility to the ion outlet.

2. A method according to claim 1 wherein the differential mobility analyser apparatus is configured and set up in accordance with a first convoluting criterion that defines the relationship between the sample gas flow rate, sheath gas flow rate, the length of the ion-separation separation chamber and the width of the focusing chamber as follows:

$$(Hin/L)*(Qsh/Qi)>Pf$$

where Hin is the width of the focusing chamber, L is the length of the ion separation chamber, Qsh is the sheath gas flow rate, Qi is the sample gas flow rate and Pf is a focusing factor which lies within the limits 1<Pf<30.

3. A method according to claim 1 wherein the focusing chamber is oriented at an angle of from 45° to 90° relative to the direction of flow of the sheath gas along the ion-separation chamber.

4. A method according to claim 3 wherein the focusing chamber is oriented at an angle of approximately 90° relative to the direction of flow of the sheath gas along the ion-separation chamber.

5. A differential mobility analyser apparatus for separating and collecting ions of a predetermined ion mobility from a gaseous mixture of ions of different ion mobilities using a differential mobility analyser apparatus, wherein the differential mobility analyser apparatus comprises an ion-separation chamber having:
    (a) a focusing chamber connected or connectable to a supply of sample gas containing ions of interest;
    (b) a sheath gas inlet connected or connectable to a supply of sheath gas;
    (b) a sheath gas outlet;
    (c) an ion outlet through which the ions of predetermined ion mobility can be quantified or collected; and
    (d) two or more electrodes arranged to provide an ion-separating electric field across the ion-separation chamber;
wherein the sample gas inlet is oriented at an angle of from 30° to 90° relative to a direction of flow of the sheath gas along the ion-separation chamber;

and wherein the apparatus is configured to provide a focusing zone in the focusing chamber, the focusing zone comprising at least two surfaces where a non-uniform density of electric charge is created so as to generate a non-uniform electric field that modifies ion trajectories in a sample gas passing through the focusing chamber and through the focusing zone so that they converge to produce an ion stream of reduced width;

the apparatus comprising a controller that enables the ion-separating electric field to be varied to attract ions of a predetermined ion mobility to the ion outlet.

6. A differential mobility analyser apparatus according to claim 5 which is configured and set up in accordance with a first convoluting criterion that defines the relationship between a sample gas flow rate, sheath gas flow rate, the length of the ion-separation chamber and the width of the focusing chamber as follows:

$$(Hin/L)*(Qsh/Qi)>Pf$$

where Hin is the width of the focusing chamber, L is the length of the ion separation chamber, Qsh is the sheath gas flow rate, Qi is the sample gas flow rate and Pf is a focusing factor which lies within the limits $1<Pf<30$.

7. A differential mobility analyser apparatus according to claim 5 wherein the focusing chamber is oriented at an angle of from 45° to 90° relative to the direction of flow of the sheath gas along the ion-separation chamber.

8. A differential mobility analyser apparatus according to claim 7 wherein the focusing chamber is oriented at an angle of approximately 90° relative to the direction of flow of the sheath gas along the ion-separation chamber.

9. A differential mobility analyser apparatus according to claim 5 wherein the focusing chamber is provided with an electrically conductive strip located in a wall thereof, wherein the electrically conductive strip has a potential difference ΔVin applied thereto, thereby to generate a focusing electric field, the strip being insulated by a surrounding electrical insulator from any other internal conductive surfaces of the focusing chamber.

10. A differential mobility analyser apparatus according to claim 5 wherein the focusing chamber is provided with a plurality of electrically conductive strips located in a wall thereof, wherein each electrically conductive strip has a potential difference ΔVin applied thereto, thereby to generate a focusing electric field, each strip being insulated by a surrounding electrical insulator from any other conductive strips and internal conductive surfaces of the focusing chamber.

11. A differential mobility analyser apparatus according to claim 5 wherein the focusing chamber is provided on an internal surface thereof with a layer of a conductive material which is insulated from the electrodes of the ion-separation chamber by an electrical insulator material and wherein a pair of conductive electrodes is connected to the conductive material and said electrodes are in turn connected to a potential difference source so as to create a desired potential along the internal surface of the focusing chamber.

12. A differential mobility analyser apparatus according to claim 11 wherein the layer of conductive material is formed from a layer of metal or a metal alloy.

13. A differential mobility analyser apparatus according to claim 12 wherein the layer of conductive material is formed from a nickel alloy.

14. A differential mobility analyser apparatus according to claim 13 wherein the nickel allow is a nickel chromium alloy.

15. A differential mobility analyser apparatus according to claim 11 wherein the layer of conductive material has been formed by application of conductive material to a substrate by means of metal-plating, vacuum deposition or painting with a conductive paint.

16. A differential mobility analyser apparatus according to claim 5 wherein the two or more electrodes (d) are formed from stainless steel and are spaced apart by a PTFE spacer.

17. A differential mobility analyser apparatus according to claim 5 wherein a baffle (guide wall) is provided adjacent the ion outlet in the ion-separation chamber, the baffle serving to guide sample gas containing ions of a predetermined ion mobility to the ion outlet.

* * * * *